United States Patent [19]

McEwen

[11] Patent Number: 5,312,431
[45] Date of Patent: May 17, 1994

[54] OCCLUSIVE CUFF
[75] Inventor: James A. McEwen, Richmond, Canada
[73] Assignee: Abatis Medical Technologies Limited, Limerick, Ireland
[21] Appl. No.: 767,812
[22] Filed: Sep. 30, 1991
[51] Int. Cl.$^5$ .............................................. A61B 17/00
[52] U.S. Cl. ................................... 606/202; 128/672
[58] Field of Search ............... 606/202, 203, 204, 201; 128/672, 677

[56] References Cited

U.S. PATENT DOCUMENTS

| | | | |
|---|---|---|---|
| 2,031,870 | 4/1934 | Vertuno | 128/327 |
| 2,444,161 | 6/1948 | Hanafin | 606/202 |
| 3,095,873 | 7/1963 | Edmunds | 128/2.05 |
| 3,120,846 | 9/1964 | Fletcher | 606/202 |
| 3,467,077 | 6/1966 | Cohen | 606/202 |
| 3,504,675 | 4/1970 | Bishop, Jr. | 606/202 |
| 3,670,735 | 6/1972 | Hazlewood | 128/327 |
| 3,825,008 | 7/1974 | Shook | 606/202 |
| 4,399,809 | 8/1983 | Baro et al. | 606/202 |
| 4,469,099 | 9/1984 | McEwen | 128/327 |
| 4,479,494 | 10/1984 | McEwen | 128/327 |
| 4,605,010 | 8/1986 | McEwen | 128/686 |
| 4,635,635 | 1/1987 | Robinette-Lehman | 128/327 |
| 4,637,394 | 1/1987 | Racz et al. | 128/327 |
| 4,770,175 | 9/1988 | McEwen | 128/327 |
| 4,869,265 | 9/1989 | McEwen | 128/774 |
| 4,979,953 | 12/1990 | Spence | 606/202 |
| 5,048,536 | 9/1991 | McEwen | 128/748 |

FOREIGN PATENT DOCUMENTS

| | | |
|---|---|---|
| 0264848 | 4/1988 | European Pat. Off. |
| 695842 | 12/1930 | France |
| 2204388 | 5/1974 | France |
| 0290046 | 8/1935 | Italy .................................. 606/202 |

OTHER PUBLICATIONS

PCT International Search Report for International Application No. PCT/IE 92/00005 dated Jan. 5, 1993.
CPC Couplings are Designed for Small Flexible Tubing Applications Publication, 3 pp. Date unavailable.
J. A. McEwen and R. W. McGraw, "An adaptive tourniquet for improved safety in surgery"; IEEE Trans. Bio-Med Eng., vol. BME29, 1982, pp. 122-128.
J. A. McEwen and G. F. Auchinleck, "Advances in Surgical Tourniquets," J.A.O.R.N., vol. 36, 1982, pp. 889-896.
J. A. Shaw and D. G. Murray, "The relationship between tourniquet pressure and . . . " J. Bone & Joint Surg., vol. 64-A, 1982, pp. 1148-1152.
A. C. McLaren and C. H. Rorabeck, "The pressure distribution under tourniquets," J. Bone & Joint Surg., 67A, pp. 433-438.
R. J. Newman and A. Muirhead, "A safe & effective low press tourniquet", J. Bone & Joint Surg., 68B, 1986, pp. 625-628.
J. S. Shaw et al., "Guidelines for the use of digital tourniquets . . . " J. Bone & Joint Surg., 67A, 1985, pp. 1086-1090.
S. E. Grice et al., "Intravenous regional anesthesia:evaluation and prevention of leakage . . . ", Anesthesiology, 65, pp. 316-320, 1986.
M. J. Breault et al., "Internal Pressure Distribution . . . ", Proc. Can. Med. Biol. Eng. Conf. (Toronto), 1989, pp. 47-49.
J. A. McEwen et al, "Development and Evaluation of . . . ", Proc. 15th Can. Med. Biol. Eng. Conf. (Toronto), 1989, pp. 107-108.

Primary Examiner—Edgar S. Burr
Assistant Examiner—Anthony H. Nguyen
Attorney, Agent, or Firm—Klarquist Sparkman Campbell Leigh & Whinston

[57] ABSTRACT

An overlapping occlusive cuff for improved application of pressure to the limb, comprising: an inflatable bladder; a sheath for containing the inflatable bladder wherein the sheath has a length sufficient to encircle the limb and overlap on itself in a substantially circumferential direction around the limb; sheath securing means for securing the overlapped sheath around the limb; and stiffening means for superimposing over a region of the overlapped and secured sheath to constrain the shape of the sheath beneath the region when the bladder is inflated. The stiffening means includes securing means for securing the overlapping sheath in a substantially circumferential direction around the limb independently of the sheath securing means such that the sheath remains overlapped and secured in a substantially circumferential direction if the sheath securing means is not engaged or becomes ineffective while the bladder is inflated.

3 Claims, 4 Drawing Sheets

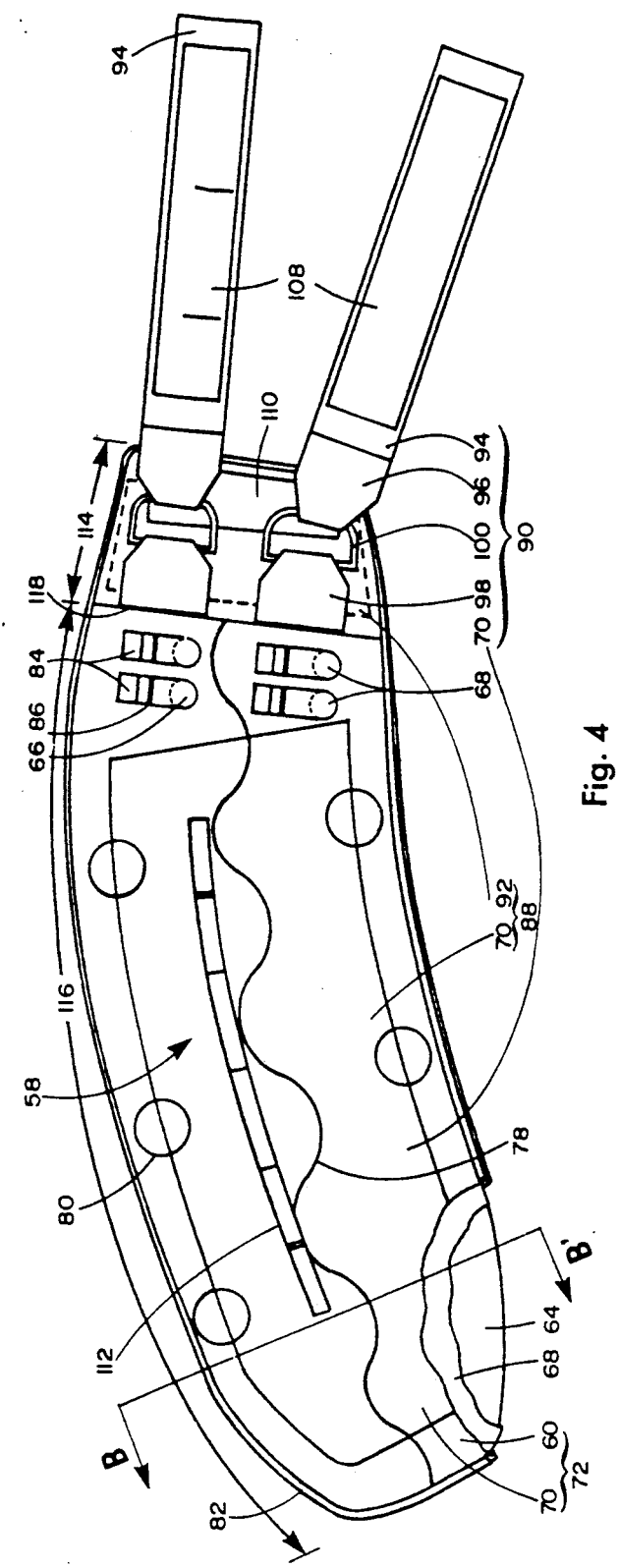
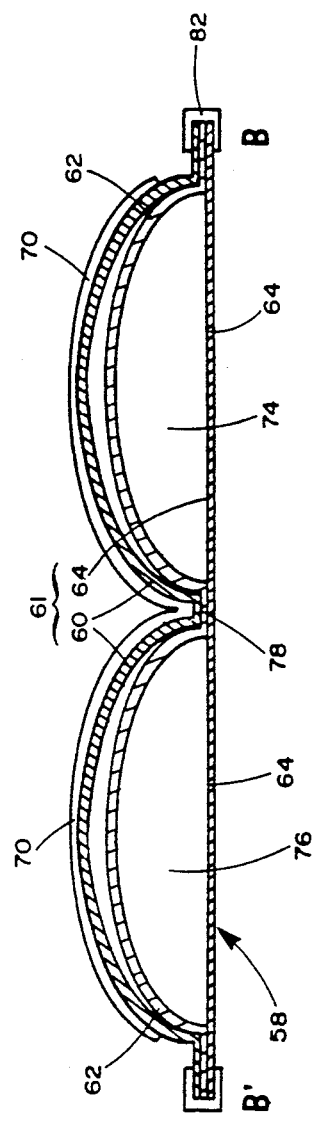

OCCLUSIVE CUFF

FIELD OF THE INVENTION

This invention pertains to cuffs for occluding flow in blood vessels in human limbs encircled by the cuffs. The invention particularly pertains to an overlapping occlusive cuff for improved application of pressure to a limb in order to facilitate the performance of a surgical procedure, comprising: an inflatable bladder; a sheath for containing the inflatable bladder wherein the sheath has a length sufficient to encircle the limb and overlap upon itself in a substantially circumferential direction around the limb; sheath securing means for securing the overlapped sheath around the limb; and stiffening means for superimposing over a region of the overlapped and secured sheath to constrain the shape of the sheath beneath the region when the bladder is inflated. The stiffening means may include securing means for securing the overlapping sheath in a substantially circumferential direction around the limb independently of the sheath securing means such that the sheath remains overlapped and secured in a substantially circumferential direction if the sheath securing means is not engaged or becomes ineffective while the bladder is inflated.

BACKGROUND OF THE INVENTION

The use of an inflatable cuff to occlude blood flow into a subject's limb, thereby providing a bloodless surgical field in the portion of the limb distal to the cuff over a time period suitably long for the performance of a surgical procedure, is well known in surgical practice. When employed to provide a bloodless surgical field, occlusive cuffs constitute one element of a surgical tourniquet system. Tourniquet systems typically include the following basic elements: a source of pressurized gas, an inflatable cuff for encircling a limb at a selected location, and a pressure regulating mechanism for controlling and maintaining the pressure of gas in the inflatable cuff and thus the pressure applied by the cuff to the limb which the cuff encircles. The recent advent of automatic tourniquet systems which employ digital electronic technology in the regulation of pressure and in the detection of certain hazardous conditions has led to significant improvements in the safety and accuracy of surgical procedures performed with an occlusive cuff applied proximally on a limb. These automatic tourniquet systems typically allow the surgeon to safely maintain a constant inflation pressure in the inflatable cuff which he or she estimates to apply pressures to the limb near the minimum required to safely occlude blood flow past the cuff. Recently, McEwen has described, in the U.S. patents and patent applications cited below, improved automatic tourniquet systems which provide for sensing and regulation of the pressures actually applied to the limb by a cuff, in contrast to merely sensing and regulation of the inflation pressure in the cuff.

However, despite improvements in electronic pressure regulation and applied pressure sensing, major limitations exist with respect to safety and efficacy of occlusive cuffs used as part of automatic tourniquet systems. These limitations in prior art occlusive cuffs have persisted despite the increasing use of such cuffs in more demanding surgical procedures, particularly those involving the use of intravenous regional anesthesia (IVRA). In surgical procedures performed under IVRA, the occlusive cuff must be effective in preventing the flow of blood into the field of surgical dissection as well as preventing the premature release of potentially toxic intravenous anesthetics from the veins of the operative limb into the general circulation.

In the design of most prior art cuffs, little attention has been paid to the actual spatial distribution of pressures applied to the limb beneath the cuffs, in both a circumferential direction around the limb, and a direction along the longitudinal axis of the limb, when the cuffs are inflated to various inflation pressures. This lack of attention has largely been due to the lack of suitable pressure transducers for measuring the applied pressures. However, in connection with the present invention, the biomedical pressure transducer described by McEwen in U.S. Pat. No. 4,869,265 was used as a tool to evaluate the ranges of pressures applied to limbs by a large number of prior art cuffs, and was used as a tool in the development and evaluation of the improved occlusive cuff described hereunder.

By using the McEwen biomedical pressure transducer to measure the pressures applied by a representative selection of prior art cuffs which overlap on themselves around limbs, major variations were found in the pressures applied in a circumferential direction around the limbs beneath the cuffs. In particular, the greatest pressure variations were found in the region of the overlap, where the pressure actually applied to the limb could be much less than the inflation pressure of the cuffs, thus creating low pressure pathways longitudinally for arterial blood to enter the limb, or for IVRA anesthetic agents to exit the limb. Significantly, prior art cuffs having the greatest cross-sectional thicknesses were found to create the greatest pressure discontinuities in the region of the overlap, and cuffs having less cross-sectional thicknesses had less pressure variations circumferentially in the region of the overlap.

Also by using the McEwen biomedical pressure transducer, it was possible to measure the pressures applied to limbs beneath prior art cuffs in a longitudinal direction along the limb, between the proximal and distal edges of the cuff, at selected locations around the circumference. Again, significant differences in longitudinally applied pressures were found in prior art cuffs having different designs. Despite the information in the prior art that shows that the magnitude and distribution of pressures longitudinally beneath cuffs affects the probability of nerve injury beneath the cuff, little attention has previously been paid to the design of cuffs which permit optimal, desirable or selectable distributions of pressures to be applied in a longitudinal direction beneath such prior art cuffs.

Limitations also exist in the safety of prior art cuffs. At present, overlapping occlusive cuffs known in the prior art generally incorporate a single means of securing the cuff around the limb, with no additional securing means functioning independently to hold the cuff in place should the first securing means fail. No overlapping cuff in the prior art known to the applicant has a secondary circumferential securing means for independently securing the overlapped cuff circumferentially around a limb so that, if the primary means for securing the cuff around the limb were to fail for any of a variety reasons, the overlapped cuff would continue to apply pressure to the limb safely for the period required to complete a surgical procedure. Almost all cuffs in the prior art are designed to overlap on themselves around limbs, and use only a primary securing means, such as a pair of mating strips of hook and loop material, for securing circumferentially. Dual-bladder cuffs known in the prior art for use in IVRA do use two separate sets of securing means, but they are intended for securing two separate bladders arranged longitudinally on the limb; if one of these sets of securing means fails, the safety and efficacy of the inflatable bladder beneath that set of strips is significantly affected. The absence of an independent, secondary circumferential securing means in overlapping cuffs of the prior art significantly limits their safety, especially in critical surgical procedures where continued maintenance of a bloodless field is essential, and in other procedures involving IVRA where the cuff must keep anesthetic agents in the limb and out of systemic circulation for a specified minimum time period.

Overlapping occlusive cuffs in the prior art generally include a stiffener cut from a sheet of flexible thermoplastic material such as polyethylene, polypropylene, or nylon, to constrain the bladder of the cuff, reduce the tendency of the inflated cuff to roll distally down the limb, and direct inflation inwardly toward the limb when the bladder is pressurized. The choice of materials and the physical dimensions of prior art stiffeners have often bee arbitrary, or based on factors other than how the physical characteristics of these stiffeners would affect the pressures applied longitudinally and circumferentially to underlying limbs. Also, such prior art stiffeners have generally been integrated physically into the cuffs during manufacture so that, in cross-section, the stiffeners represent one integral layer of a multi-layer structure. One result is that such prior art cuffs have significant cross-sectional thickness, producing significant applied pressure discontinuities in their overlapping regions, as described above. Such prior art cuffs are relatively rigid longitudinally across their width dimension, which limits their conformance to different limb shapes and can produce undesirable longitudinal pressure distributions. Also, such prior art cuffs are relatively rigid along their length, which increases the difficulty that clinical staff have in attempting to bend such cuffs around limbs to snugly encircle them.

Most cuffs of the prior art employ Luer-type connectors to attach the cuffs to tubing connected to the pressure regulators of automated tourniquet systems. These Luer-type connectors have inherent safety limitations, because they have no secondary locking mechanism and they permit easy, inadvertent gas leaks and disconnection as a result of rotation of the tubing with respect to the cuff. Further safety limitations of overlapping cuffs of the prior art related to the absence of markings on the cuffs indicating aspects of the recommended, safe and efficacious use of the cuffs. For example, most prior art cuffs do not include markings which provide guidance as to the best choice of cuff, taking into account the shape, circumference and available length of a patient's limb, nor are markings generally included to assist in the optimal setting of inflation pressure or proper cuff usage.

An object of the present invention is to provide an overlapping occlusive cuff having secondary safety securing means for improved safety, comprising: an inflatable bladder for encircling and overlapping on itself around a limb, bladder securing means for engaging to secure the overlapping bladder around the limb with the bladder inflated to a pressure sufficient to occlude flow in blood vessels in the limb encircled by the bladder, and secondary safety securing means for securing the overlapping bladder around the limb independently of the bladder securing means such that the bladder remains overlapped and secured if the bladder securing means is not engaged or becomes ineffective while the bladder is inflated. A related object is to provide an operator with a visible indication on the cuff of a parameter affecting the safety or efficacy of the cuff, such as which cuff to select for best performance, or what inflation pressure is recommended, in a particular situation. Another related object for improved safety is to provide a cuff with locking connector means to connect the inflatable bladder to a tube containing pressurized gas while allowing bidirectional rotation of the tube with respect to the bladder until an operator disconnects the bladder from the tube by a combination of manual actuations.

Another object of the present invention is to provide an overlapping occlusive cuff having separately overlapping bladder and stiffener for improved application of pressure in a substantially circumferential direction around the limb, comprising: an inflatable bladder with a length sufficient for encircling and overlapping on itself around the limb, bladder securing means for securing the overlapping bladder around the limb, and stiffening means superimposed on the overlapping region of the bladder for directing the bladder in that region toward the limb when the bladder is inflated. A related object is to fabricate the stiffening means from flexible material such as hook and loop fastening strips so that the stiffening means can also function as a secondary safety securing means.

A further object of the present invention is to provide an improved occlusive cuff having partial fluting to reduce the tendency of the cuff to roll, comprising: an inflatable bladder formed from two sheets of flexible plastic material of substantially the sam size and shape and having proximal and distal side edges and two end edges and sealed along the edges to form an inflatable space, and having a length sufficient for the bladder to encircle the limb at a desired location and overlap on itself around the limb; bladder securing means for securing the overlapping bladder around the limb while the bladder is inflated; and partial fluting means comprised of a number of seams which further join together the two sheets of plastic material forming the bladder, and which have preselected locations, distances from the end edges, and lengths from the respective side edges to constrain the shape of the bladder, thereby reducing the tendency of the bladder to roll along the longitudinal axis of the limb when inflated The applicant is aware of the following U. S. patents which are more or less relevant to the subject matter of the applicant's invention.

| 5,048,536 | 9/1991 | McEwen | 128/748 | |
| 4,869,265 | 9/1989 | McEwen | 128/774 | 128/327 |
| 4,770,175 | 9/1988 | McEwen | 128/327 | |
| 4,605,010 | 8/1986 | McEwen | 128/686 | |
| 4,479,494 | 10/1984 | McEwen | 128/327 | 128/682 |
| 4,469,099 | 9/1984 | McEwen | 128/327 | 128/682 |

The applicant is also aware of the following U.S. patent applications which are more or less relevant to the subject matter of the applicant's invention.

Applicant: J. A. McEwen; Title: Improved Tourniquet for Sensing and Regulation of Applied Pressures; Filing Date: Sep. 13, 1991; Serial Number: Not Yet Available.

Applicant: J. A. McEwen; Title: Tourniquet Apparatus for Intravenous Regional Anesthesia; Filing Date: Jan. 29, 1990; Ser. No. 07/471,514.

The applicant is also aware of the following published references which are more or less relevant to the subject matter of the applicant's invention.

M. J. Breault, B. Graham, J. A. McEwen and R. W. McGraw, "Internal pressure distribution in limbs encircled by pneumatic surgical tourniquets." Proceedings of the Canadian Medical and Biological Engineering Conference (Toronto, Canada), 1989, pp. 47–49.

J. A. McEwen, M. J. Breault and C. L. Park, "Development and evaluation of calibrated tourniquet cuffs." Proceedings of the Canadian Medical and Biological Engineering Conference (Toronto, Canada), 1989, pp. 107–108.

J. A. McEwen and R. W. McGraw, "An adaptive tourniquet for improved safety in surgery." IEEE Transactions in Biomedical Engineering, Vol.BME-29, February 1982, pp. 122–128.

J. A. McEwen and G. F. Auchinleck, "Advances in surgical tourniquets." J. Assn. Operating Room Nurses, Vol. 36, 1982, pp. 889–896.

J. A. Shaw and D. G. Murray, "The relationship between tourniquet pressure and underlying soft-tissue pressure in the thigh." The Journal of Bone and Joint Surgery, Vol. 64-A, 1982, pp. 1148–1152.

A. C. McLaren and C. H. Rorabeck, "The pressure distribution under tourniquets." The Journal of Bone and Joint Surgery, Vol. 67-A, 1985, pp. 433–438.

R. J. Newman and A. Muirhead, "A safe and effective low pressure tourniquet." Journal of Bone and Joint Surgery, Vol. 68-B, 1986, pp. 625–628.

J. A. Shaw, W. W. Demuth, and A. W. Gillespy, "Guidelines for the use of digital tourniquets based on physiological pressure measurements." The Journal of Bone and Joint Surgery, Vol. 67-A, 1985, pp. 1086–1090.

S. E. Grice et al., "Intravenous regional anesthesia: Evaluation and prevention of leakage under the tourniquet." Anesthesiology, Vol. 65, pp. 316–320, 1986.

SUMMARY OF THE INVENTION

The invention is directed toward an overlapping occlusive cuff for improved application of pressure to the limb, comprising: an inflatable bladder; a sheath for containing the inflatable bladder wherein the sheath has a length sufficient to encircle the limb and overlap on itself in a substantially circumferential direction around the limb; sheath securing means for securing the overlapped sheath around the limb; and stiffening means for superimposing over a region of the overlapped and secured sheath to constrain the shape of the sheath beneath the region when the bladder is inflated.

The invention is further directed toward an overlapping occlusive cuff having secondary safety securing means for improved safety, comprising: an inflatable bladder for encircling a limb, wherein the length of the bladder is sufficient for the bladder to encircle the limb at a desired location and overlap on itself circumferentially around the limb; bladder securing means for engaging to secure the overlapping bladder in a substantially circumferential direction around the limb for the duration of a surgical procedure with the bladder inflated to a pressure sufficient to occlude flow in blood vessels in the limb encircled by the bladder; and secondary safety securing means for securing the overlapping bladder in a substantially circumferential direction around the limb independently of the bladder securing means such that the bladder remains overlapped and secured in a substantially circumferential direction if the bladder securing means is not engaged or becomes ineffective while the bladder is inflated. The cuff may include marking means to provide a visible indication of a parameter affecting the safety or efficacy of the cuff. The cuff may also include locking connector means having a connecting element to connect the bladder to a tube containing pressurized gas by pushing the tube into the connecting element, thereby establishing a gas passageway, and having a locking element with release means for locking the bladder and the tube together and maintaining the passageway, while allowing bidirectional rotation of the tube with respect to the connecting element, until an operator disconnects the bladder from the tube by manually actuating the release means of the locking element while simultaneously pulling the tube from the connecting element.

The invention is further directed toward an improved occlusive cuff having partial fluting means to reduce the tendency of the cuff to roll, comprising: an inflatable bladder formed from two sheets of flexible plastic material of substantially the same size and shape and having proximal and distal side edges and two end edges and sealed along the edges to form an inflatable space, and wherein the length of the bladder along the proximal and distal side edges is sufficient for the bladder to encircle the limb at a desired location and overlap on itself in a substantially circumferential direction around the limb; partial fluting means comprised of a plurality of seams located at preselected distances from the two end edges of the bladder and extending for preselected lengths from the seals along the proximal and distal side edges of the bladder, whereby the seams further join together the two sheets of plastic material forming the bladder; and bladder securing means for securing the overlapping bladder in a substantially circumferential direction around the limb while the bladder is inflated to a pressure sufficient to occlude flow in blood vessels in the limb encircled by the bladder for the duration of a surgical procedure. The plurality of seams may have preselected locations, distances from the end edges, and lengths from the respective side edges to constrain the shape of the bladder, thereby reducing the tendency of the bladder to roll along the longitudinal axis of the limb when inflated

BRIEF DESCRIPTION OF THE DRAWINGS

A specific embodiment of this invention has been chosen for purposes of illustration and description wherein.

An alternate embodiment of this invention has been included for purposes of illustration and description wherein:

FIG. 4 is a plan view of the alternate embodiment of the improved overlapping occlusive cuff for application to a limb substantially conical in shape.

FIG. 5 is a cross-sectional view of the overlapping occlusive cuff of FIG. 4 taken along line B—B'.

Figure 6:
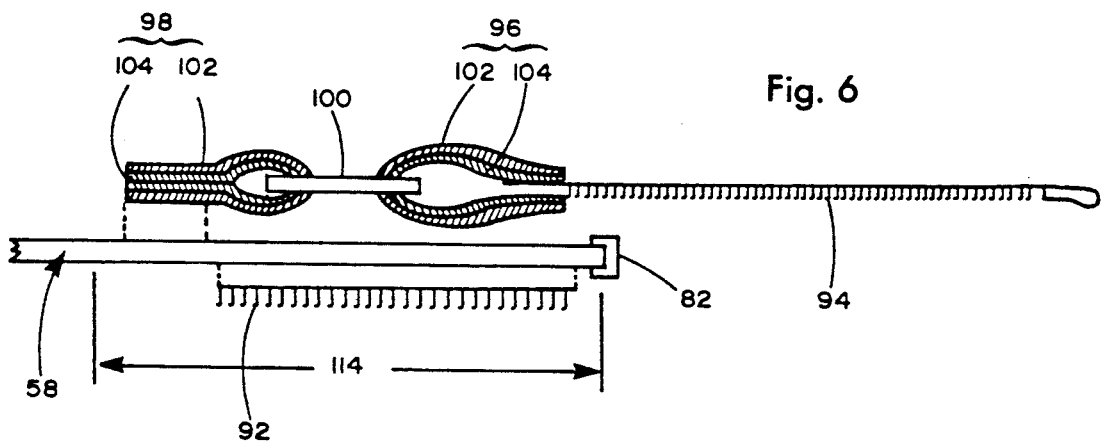

FIG. 6 is an exploded view of pivoting secondary safety securing means assembly of the cuff shown in FIG. 4.

Figure 7:
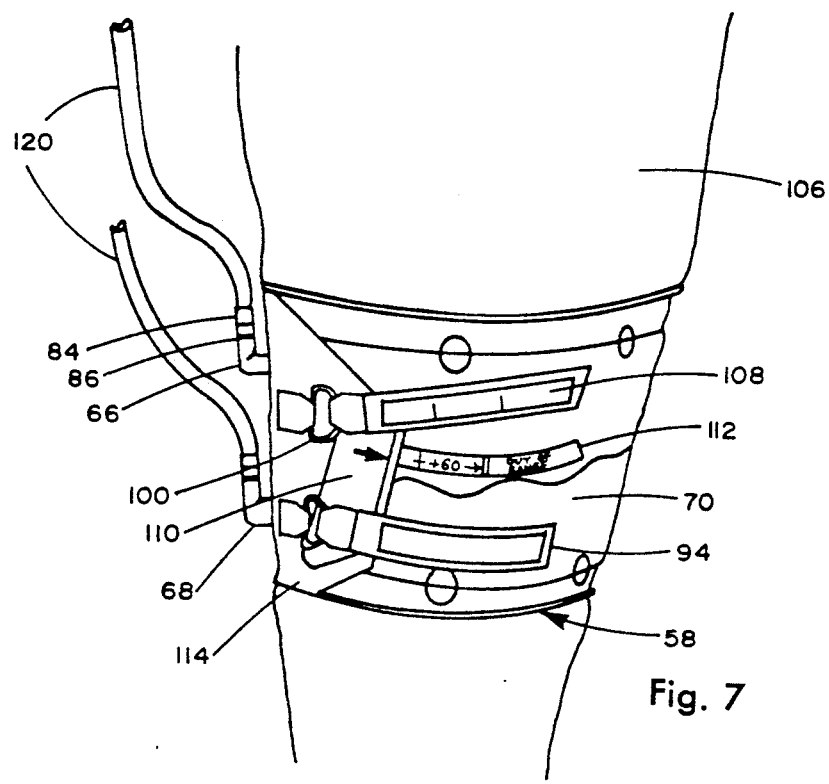

FIG. 7 is pictorial representation of the cuff, secondary safety securing means and markings shown in FIG. 4 as applied to a patient's limb.

DESCRIPTION OF THE SPECIFIC EMBODIMENT

The specific embodiment illustrated is not intended to be exhaustive or to limit the invention to the precise form disclosed. It is chosen and described in order to explain the principles of the invention and its application and practical use, and thereby enable others skilled in the art to utilize the invention.

Figure 1:
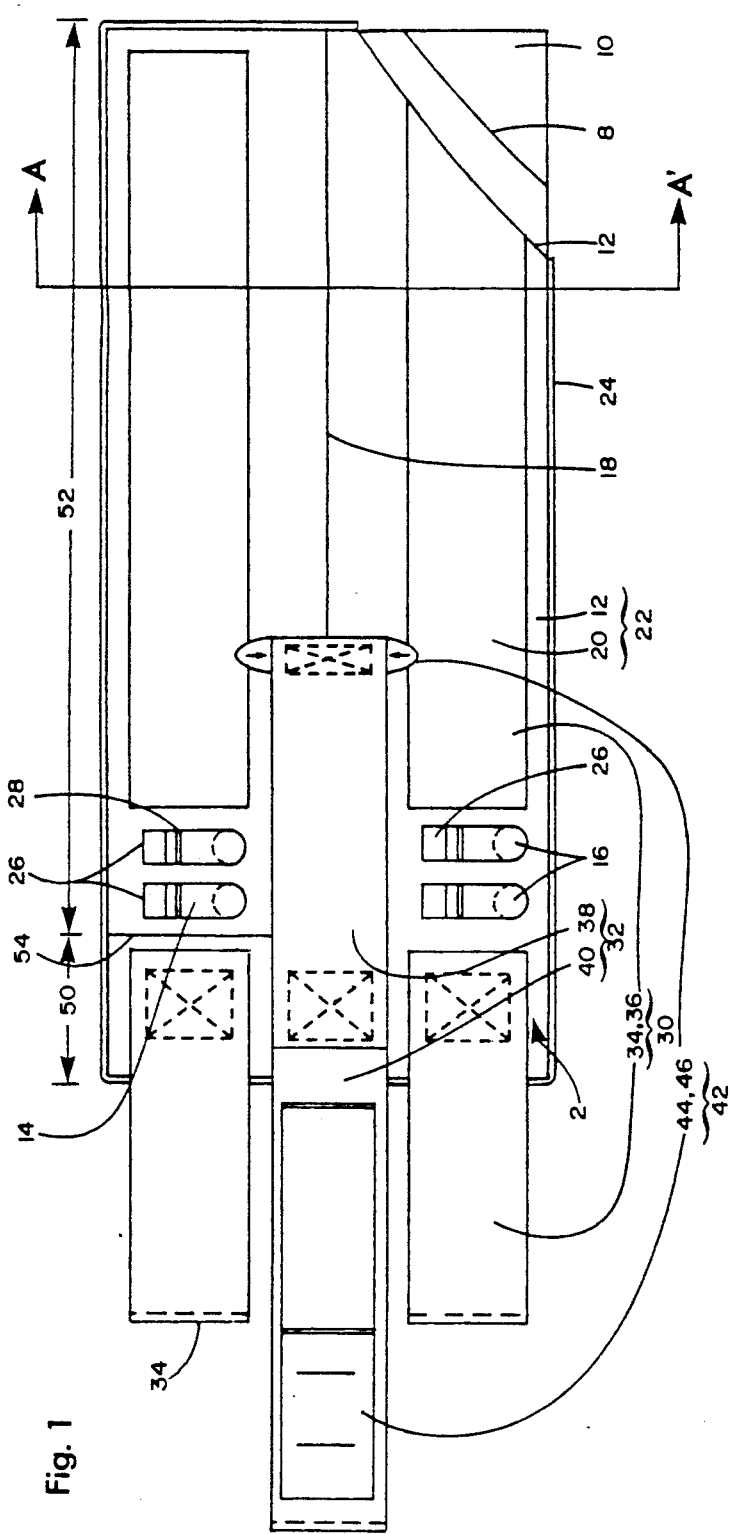
FIG. 1 is a plan view of the specific embodiment of the improved overlapping occlusive cuff for application to a limb substantially cylindrical in shape.

FIG. 1 is a plan view illustrating details of an overlapping occlusive cuff 2 having secondary safety securing means for improved safety. Cuff 2 is designed for best shape conformance to limbs substantially cylindrical in shape. Design and fabrication of cuff 2 is similar in certain respects to the design and fabrication of the invention disclosed by Robinette-Lehman in U.S. Pat. No. 4,635,635, but with a number of significant improvements resulting in enhanced safety, efficacy and cost-effectiveness, as herebelow described.

Also, Robinette-Lehman in U.S. Pat. No. 4,635,635 discloses six cuff sizes whereas, cuff 2 is fabricated in sizes of different length and in a variety of widths to fit 95% of the normal adult size range, so that the surgeon may optimally select cuff 2 by length and width depending on the patient's limb circumference, limb length and the surgical procedure.

As shown in FIG. 1, cuff 2 comprises inflatable bladders 4 and 6 having proximal and distal sides and two ends, wherein the length of the proximal and distal sides is sufficient for the bladder to encircle the limb at a desired location and overlap on itself in a substantially circumferential direction around the limb. Inflatable bladders 4 and 6 are contained in sheath 11 formed by layers 10 and 12, wherein the length of sheath 11 is sufficient for sheath 11 to encircle the limb at a desired location and overlap on itself in a substantially circumferential direction around the limb. Cuff 2 is fabricated using only three layers 8, 10 and 12 and has no internal thermoplastic stiffener. This characteristic results in a cuff design that is thinner and more flexible improving the performance of cuff 2 by providing a more uniform applied pressure to the limb in both the longitudinal axis along the limb as well as at the point where bladders 4 and 6 overlap reducing the number of potential paths for blood flow. This characteristic makes cuff 2 more suitable for pediatric patients with small limb circumferences than other cuffs which are thicker in cross-section. Layers 8, 10 and 12 of cuff 2 are fabricated from a flexible gas-impermeable synthetic cloth, such as a woven nylon backed with a thermoplastic polyurethane coating. This material is substantially inextensible when cuff 2 is pressurized up to 500 mmHg. Layer 12 and bottom layer are coated with polyurethane on one side only and inside layer 8 is coated on both sides. Thermoplastic coatings on layers 8, 10 and 12 facilitate bonding or "heat sealing" in fabrication of cuff 2. The woven nylon surface of layer 10 is a soft, non-wrinkling material. Use of this softer material makes the wider embodiments of cuff 2 more comparable to blood pressure cuffs than other cuffs employing less compliant materials.

The materials and fabrication technique of cuff 2 make it economically suitable for limited re-use applications. Other materials for layers 8, 10, and 12 such as flexible thermoplastic polyvinylchloride (PVC) sheeting may be readily substituted for design transferability of cuff 2 to disposable applications in which cuff 2 may be sterile or non-sterile.

Valve sets 14 and 16 consists of two thermoplastic right-angle valves. With respect to valve sets 14 and 16, one port of the set may serve as an opening for cuff inflation and deflation while the other port of the set may be used for sensing the gas pressure within cuff 2. This feature allows the surgical tourniquet system to detect pressure drops and occluding kinks in the pneumatic hose connecting the tourniquet regulator and cuff 2.

Figure 2:
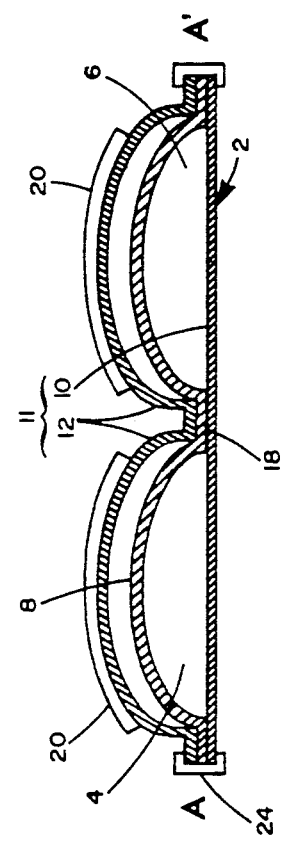
FIG. 2 is a cross-sectional view of the overlapping occlusive cuff of FIG. 1 taken along line A—A'.

Gas-impermeable inflation bladders 4 and 6 of cuff 2 are formed with bladder dividing heat seal 18 as illustrated in FIG. 2. Inflation bladders 4 and 6 form an integral part of cuff 2 and are not removable. Consequently, in cleaning and inspecting cuff 2 for re-use, errors in re-assembly which can affect safety and performance of cuff 2 have been eliminated.

Inclusion of bladder dividing heat seal 18 results in dual-bladder cuff 2 with bladder 4 permanently isolated from bladder 6. As shown in FIGS. 1 and 2, fluid access to bladder 4 is achieved by valve set 14 while fluid access to bladder 6 is through valve set 16. In another embodiment of the invention, omission of bladder dividing heat seal 18 results in a single-bladder cuff with one bladder 4. For the single-bladder cuff, fluid access to bladder 4 is achieved by valve set 14 as valve set 16 is omitted.

Referring to FIG. 1, loop material 20 on top layer 12 provides stiffening means in the form of compliant stiffening layer 22 comprised of woven plastic fibers and located above a segment of the overlapped bladders 4, 6 which covers the end of the overlapped bladders 4, 6 that is in closest proximity to the limb, for directing the bladder in the region of the overlap toward the limb when bladders 4, 6 are inflated. Stiffening layer 22 also secures sheath 11 around the limb when bladder 4 or 6 is inflated to a pressure sufficient to stop blood flow in the limb encircled by cuff 2. Layer 22 has a width dimension and a length dimension sufficient for encircling bladders 4 and 6 around the limb. The stiffness of layer 22 can by varied by selecting woven plastic fibers of different thickness and rigidity. The predetermined stiffness of layer 22 directs the portion of the bladder beneath layer 22 toward the limb to produce an applied pressure at predetermined levels near a plurality of predetermined locations on the limb beneath bladders 4 and 6 when bladders 4 and 6 are inflated. This arrangement is chosen to achieve a desired applied pressure gradient so that the risk of injury to nerves underlying cuff 2 is minimized. In addition, substitution of an internal die-cut, integrated thermoplastic stiffener with an external woven fiber stiffener layer 22 that is independent of the inflatable bladders 4 and 6 provides a cuff that is easier to apply and has superior consistency of blood flow occlusion with variations in technique of cuff application. This omission of the internal thermoplastic stiffener significantly reduces the cost to manufacture cuff 2 resulting in a cuff design that is more economical than the majority of tourniquet cuffs of the prior art.

Edge trim 24 consists of a synthetic cloth material such as nylon. Edge trim 24 protects the heat sealed areas of cuff 2 from damage in addition to preventing the rough edges of layers 8,10 and 12 from contacting the patient.

Pneumatic locking connectors 26 (PMC 26-04, Colder Products Co, St. Paul, MN) are inserted into the ports of valve sets 14 and 16. Each of the locking connectors 26 has a connecting element to connect bladders 4, 6 to a tube containing pressurized gas and a locking element with release means for locking bladders 4, 6 and the tube together. This arrangement maintains the passageway while allowing bi-directional rotation of the tube with respect to the connecting element. Luer connectors which are extensively used in prior art tourniquet cuffs are prone to accidental disconnection due to bi-directional rotation of the tube with respect to the connecting element. Use of locking connectors 26 reduce the risk of cuff deflation from accidental disconnection. Self-locking thermoplastic tie straps 28 secure connectors 26 in place.

Bladders 4 and 6 are held in place on a limb by bladder securing means 30 and secondary safety securing means 32 which are sufficient to secure bladders 4 and 6 around the limb when either bladder 4 or bladder 6 is inflated to a pressure sufficient to stop blood flow past cuff 2. Secondary safety securing means 32 functions independently of bladder securing means 30 such that bladders 4 and 6 remain overlapped and secured in a substantially circumferential direction if the bladder securing means 30 is not engaged or becomes ineffective while the bladder is inflated to a pressure sufficient to stop arterial blood flow into the limb distal to cuff 2. Bladder securing means 30 consists of hook material 34 and loop material 36. Secondary safety securing means 32, forming a separate and independent securing means from bladder securing means 30, is composed of loop material 38 and hook material 40. Hook material 40 and loop material 38 of secondary safety securing means 32 are different in color from the materials of bladder securing means 30 to distinguish secondary safety securing means 32 and to assist the user in applying cuff 2 to the patient.

Secondary safety securing means 32 also provides independent stiffening means, where each of the overlapping bladders 4 and 6 and the stiffening means overlaps on itself independently around the limb to direct the overlapped bladders 4 and 6 towards the limb and thereby improve application of pressure onto the limb beneath the overlap. This arrangement also allows the snugness of bladders 4 and 6 and snugness of the stiffening means on a limb to be selected independently by an operator. The stiffening means is comprised of woven plastic fibres having preselected stiffness. The selection of material for the stiffening means and the degree of extensibility of the material can be varied to produce applied pressures at predetermined levels near a plurality of predetermined locations on the limb beneath bladders 4 and 6 when bladders 4 and 6 are inflated.

Marking means 42 provides information useful to an operator in determining the pressure to which bladders 4 and 6 should be inflated to occlude blood flow. Marking means 42 comprises one element consisting of a set of graduated markings and another element consisting of a cursor mark whereby the value of a preselected parameter is estimated by the juxtaposition of the cursor mark and one of the set of graduated markings when the secondary safety securing means 32 is secured over the overlapping bladders 4 and 6 in a substantially circumferential direction around the limb. Marking means 42 consists of label 44 sewn to hook material 40 and pointer 46 sewn to the end of loop material 38. Pointer 46 is constructed of semi-rigid thermoplastic sheeting such as polypropylene with a thickness of approximately 1 mm and having a length sufficient to expose a printed arrow or similar indicator when second bladder securing means 32 encircles cuff 2.

Figure 3:
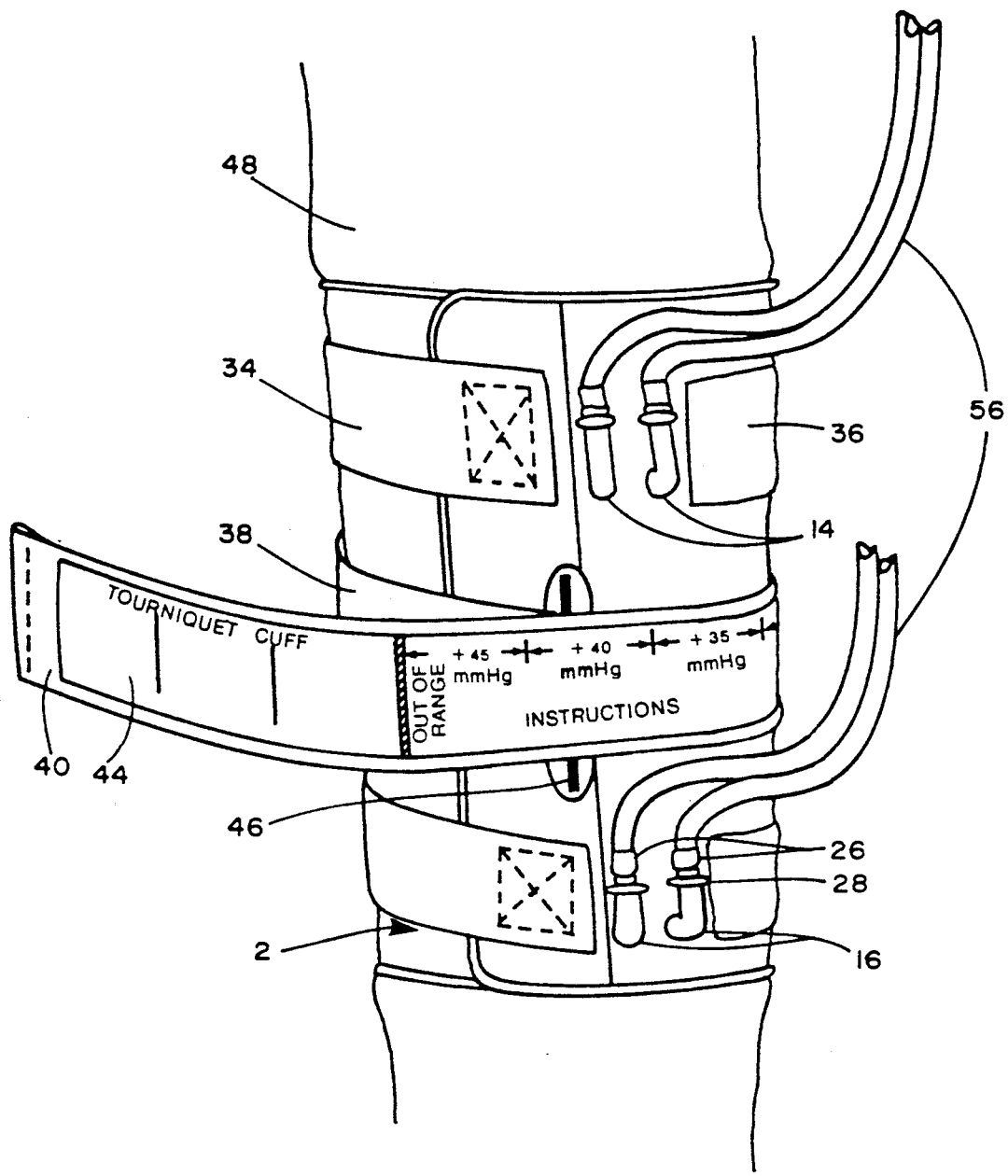
FIG. 3 is a pictorial representation of the overlapping occlusive cuff, secondary safety securing means and markings means shown in FIG. 1 as applied to a patient's limb.

FIG. 3 illustrates application of overlapping occlusive cuff 2 to substantially cylindrical limb 48. Label 44 includes markings to restrict use to properly trained staff, instructions detailing proper use of cuff 2 in intravenous regional anesthesia, index markings to identify size range or the maximum and minimum permissible limb circumferences, and a calibrated scale to indicate a recommended minimum inflation pressure for cuff 2 on limb 48. The recommended minimum inflation pressure corresponds to the lowest constant pressure normally required in cuff 2 to safely and reliably occlude blood flow over a time period suitably long for the performance of a surgical procedure when cuff 2 snugly encircles a normal limb of that circumference in a normotensive subject. This information enables the user to safely apply or determine if another tourniquet cuff size would be more appropriate for the patient and to select an inflation pressure for cuff 2 to reduce the risk of underlying nerve injury and achieve improved patient tolerance of cuff 2 when cuff 2 is pressurized.

Fabrication of the overlapping occlusive cuff 2 proceeds through manufacture of a number of subassemblies. First, layers 8, 10 and 12 are die cut from thermoplastic cloth material. At this time, circular openings are die cut into layers 8 and 12 for later passage of valve port sets 14 and 16. Loop material 20 is sewn to top layer 12 with loops facing away from layer 12. Valve sets 14 and 16 are inserted through the circular openings previously die cut into layer 8, and flanges of valve sets 14 and 16 are bonded to the bottom coated surface of layer 8 through use of radio frequency heat sealing equipment. Layers 8, 10 and 12 are then manipulated such that valve sets 14 and 16, previously bonded to layer 8, pass through the circular openings in layer 12, and the thermoplastic polyurethane coating of layer 12 contacts the upper coated surface of layer 8 and the thermoplastic polyurethane coating of layer 10 contacts the lower coated surface of layer 8. Following this step, layers 8, 10 and 12 are permanently bonded together at the peripheral edge of cuff 2, at the bladder dividing heat seal 18, and at fluid tight seal 54 through use of the radio frequency heat sealing equipment, thereby forming non-inflatable bladder section 50 and inflatable bladder section 52 contained within sheath 11 formed by layers 10 and 12. This completes the fabrication of the first subassembly.

The second subassembly, or secondary safety securing means 32, is fabricated as follows. Pointer 46 is die cut from polypropylene sheet material which has been previously silk screened with position indicators such as arrows in enamel ink. Label 44, previously silk screened with text in enamel ink, is die cut from nylon sheet material. Loop material 38 is sewn to hook material 40 such that the hooks face away from the loops and material 38 overlaps material 40 by 10 cm. Pointer 46 is then sewn to the end of loop material 38 and label 44 is sewn to the non-hook side of material 40.

In final assembly of cuff 2, edge trim 24 is first sewn around the perimeter of cuff 2 as shown in FIG. 1. Hook material 34 is sewn to the end of section 50 with the hooks facing towards layer 12. Secondary safety securing means 32 is sewn to section 50 such that the hooks of material 40 face layer 12 and the loops of material 38 face away from layer 12. The ends of hook materials 34 and 40 of bladder securing means 30 and 32 are folded over and sewn to provide a small flap for facilitating the release of bladder and secondary safety securing means 30 and 32 upon completion of the surgical procedure. Finally, connectors 26 are inserted into valve sets 14 and 16, and tie straps 28 are wrapped and tightened around valves sets 14 and 16 to secure connectors 26 in place. This completes fabrication of cuff 2.

As shown in FIG. 3, cuff 2 is applied to limb 48 with bladder securing means 30 being fastened followed by secondary safety securing means 32 being wrapped around cuff 2. Hook material 34 engages loop material 20 Adjustment of secondary safety securing means 32, which also functions as an independent stiffening means, allows the user to adjust the snugness of the stiffening means independent of the snugness of overlapped bladders 4 and 6, producing a variable spatial distribution of pressure on encircled limb 48 beneath overlapped bladders 4 and 6 of cuff 2. The user references label 44 to obtain the recommended minimum inflation pressure indicated by the position of pointer 46 with respect to calibrated scale on label 44. Should pointer 46 fall outside the calibrated scale, the user is instructed to select a different size of cuff for the patient. In FIG. 3, cuff 2 is connected by tubing 56 and connectors 26 to a pressure source providing gas at a regulated pressure between zero and 500 mmHg. This arrangement provides a means of inflating cuff 2 to apply a desired distribution of pressures to limb 48.

DESCRIPTION OF THE ALTERNATE EMBODIMENT

The alternate embodiment illustrated is not intended to be exhaustive or to limit the invention to the precise form disclosed. It is chosen and described in order to explain the principles of the invention and its application and practical use, and thereby enable others skilled in the art to utilize the invention.

FIG. 4 is a plan view of the alternate embodiment. FIG. 4 illustrates details of an overlapping occlusive tourniquet cuff 58 having secondary safety securing means for improved safety. Cuff 58 is designed for best shape conformance to limbs substantially conical in shape. As with cuff 2, cuff 58 is fabricated in a range of lengths and widths designed to fit 95% of the normal adult size range, so that the surgeon may optimally select cuff 58 by length and width depending on the patient's limb circumference, limb length and the surgical procedure.

Design and fabrication of cuff 58 is similar in certain respects to the design and fabrication of the invention disclosed by Robinette-Lehman in the U.S. Pat. No. 4,635,635, but with a number of significant improvements resulting in enhanced safety, efficacy and cost-effectiveness, as herebelow described.

FIG. 4 illustrates an inflatable overlapping occlusive tourniquet cuff 58 for application to limbs substantially conical in shape. Cuff 58 has a substantially arcuate shape with the radius of the arc passing along the width dimension. Cuff 58 has a radial length dimension of 88 cm measured along the centerline of cuff 58 and a width dimension of 20 cm perpendicular to the centerline.

As shown in FIG. 4, cuff 58 comprises inflatable bladders 74 and 76 having proximal and distal sides and two ends, wherein the length of the proximal and distal sides is sufficient for the bladder to encircle the limb at a desired location and overlap on itself in a substantially circumferential direction around the limb. Inflatable bladders 74 and 76 are contained in sheath 61 formed by layers 60 and 64, wherein the length of sheath 61 is sufficient for sheath 61 to encircle the limb at the desired location and overlap on itself in a substantially circumferential direction around the limb. Cuff 58 is fabricated using only three layers 60, 62 and 64 and has no internal thermoplastic stiffener. This characteristic results in a cuff design that is thinner and more flexible improving the performance of cuff 58 by providing a more uniform applied pressure to the limb in both the longitudinal axis along the limb as well as at the point where bladders 74 and 76 overlap reducing the number of potential paths for blood flow. This characteristic makes cuff 58 more suitable for pediatric patients with small limb circumferences than other cuffs which are thicker in cross-section. Layers 60, 62 and 64 of cuff 58 are fabricated from a flexible gas-impermeable synthetic cloth such as a woven nylon backed with a thermoplastic polyurethane coating. This material is substantially inextensible when cuff 58 is pressurized up to 500 mmHg. Layer 60 and bottom layer 64 are coated with polyurethane on one side only, and inside layer 62 is coated on both sides. Thermoplastic coatings on layers 60, 62 and 64 facilitate bonding or "heat sealing" in fabrication of cuff 58. The woven nylon surface of layer 64 is a soft, non-wrinkling material. Use of this softer material makes the wider embodiments of cuff 58 more comparable to blood pressure cuffs than other cuffs employing less compliant materials. The materials and fabrication technique of cuff 58 make it economically suitable for limited re-use applications. Other materials for layers 60, 62 and 64 such as flexible thermoplastic polyvinylchloride (PVC) sheeting may be readily substituted for design transferability of cuff 58 to disposable applications in which cuff 58 may be sterile or non-sterile.

Valve sets 66 and 68 consist of two thermoplastic right-angle valves. With respect to valve sets 66 and 68, one port of the set may serve as an opening for cuff inflation and deflation while the other port of the set may be used for sensing the gas pressure within cuff 58. This feature allows the surgical tourniquet system to detect pressure drops and occluding kinks in the pneumatic hose connecting the tourniquet regulator and cuff 58.

Gas-impermeable inflation bladders 74 and 76 of cuff 58 are formed with bladder dividing heat seal 78 as illustrated in FIG. 4. Bladder dividing heat seal 78 is an arcuate sinusoidal wave of a predefined frequency and amplitude which runs parallel to the centerline of cuff 58. Inflation bladders 74 and 76 form an integral part of cuff 58 and are not removable. Consequently, in cleaning and inspecting cuff 58 for re-use, errors in re-assembly which can affect safety and performance of cuff 2 have been eliminated.

Inclusion of bladder dividing heat seal 78 results in dual-bladder cuff 58 with bladder 74 permanently isolated from bladder 76. As shown in FIGS. 4 and 5, fluid access to bladder 74 is through valve set 66 while fluid access to bladder 76 is through valve set 68. In another embodiment of the invention, omission of heat seal 78 results in a single-bladder cuff with one bladder 74. For the single-bladder cuff, fluid access to bladder 74 is achieved by valve set 66 as valve set 68 is omitted.

Referring to FIG. 4, loop material 70 on top layer 60 provides stiffening means in the form of compliant stiffening layer 72 comprised of woven plastic fibers and located above a segment of the overlapped bladders 74 and 76. Stiffening layer 72 which covers the end of the overlapped bladders 74 and 76 that is in closest proximity to the limb directs the bladders in the region of the overlap toward the limb when bladders 74 and 76 are inflated. Stiffening layer 72 also secures sheath 61 around the limb when bladder 74 or 76 is inflated to a pressure sufficient to stop blood flow in the limb encircled by cuff 58. Layer 72 has a width dimension and a length dimension sufficient for encircling bladders 4 and 6 around the limb. The stiffness of layer 22 can by varied by selecting woven plastic fibers of different thickness and rigidity. The predetermined stiffness of layer 72 directs the portion of the bladder beneath layer 72 toward the limb to produce applied pressures at predetermined levels near a plurality of predetermined locations on the limb beneath bladders 74 and 76 when bladders 74 and 76 are inflated. The selection of materials for the stiffening means and the degree of extensibility of the material can be varied to produce a desired applied pressure on the limb. This arrangement is chosen to achieve a desired applied pressure gradient so that the risk of injury to nerves underlying cuff 58 is minimized. In addition, substitution of an internal diecut, integrated thermoplastic stiffener with an external woven fiber stiffener layer 72 that is independent of the inflatable bladders 74 and 76 provides a cuff that is easier to apply and has superior consistency of blood flow occlusion with variations in technique of cuff application. This omission of the internal thermoplastic stiffener significantly reduces the cost to manufacture cuff 58 resulting in a cuff design that is more economical than the majority of tourniquet cuffs of the prior art.

Partial fluting means comprised of a plurality of seams located at preselected distances from the two end edges of the bladders 74 and 76 controls the expansion of bladders 74 and 76 when cuff 58 is inflated. Partial flutes 80 are positioned to overlap both layer 60 and the edge of loop material 70 and are heat sealed to permanently bond layers 60, 62, 64 and 70 together thereby preventing expansion of bladders 74 and 76 within the region of the partial flutes 80. The frequency of the partial flutes 80 on the proximal and distal edges of cuff 58 reduces the tendency of cuff 58 to rolling down the limb when bladders 74 and 76 of cuff 58 are pressurized.

Edge trim 82 consisting of synthetic cloth material such as nylon. Edge trim 82 protects the heat sealed areas of cuff 58 from damage in addition to preventing the rough edges of layers 60, 62, and 64 from contacting the patient.

Pneumatic locking connectors 84 (PMC 26-04, Colder Products Co, St. Paul, Minn.) are inserted into the ports of valve sets 66 and 68. Each of the locking connectors 84 has a connecting element to connect bladders 74 and 76 to a tube containing pressurized gas and a locking element with release means for locking bladders 74 and 76 and the tube together. This arrangement maintains the passageway while allowing bi-directional rotation of the tube with respect to the connecting element. Luer connectors which are extensively used in prior art tourniquet cuffs are prone to accidental disconnection due to bi-directional rotation of the tube with respect to the connecting element. Use of locking connectors 84 reduces the risk of cuff deflation from accidental disconnection. Self-locking thermoplastic tie straps 86 secure connectors 84 in place.

Bladders 74 and 76 are held in place on a limb by bladder securing means 88 and secondary safety securing means 90 which are sufficient to secure bladders 74 and 76 around the limb when either bladder 74 or bladder 76 is inflated to a pressure sufficient to stop blood flow past cuff 58. Secondary safety securing means 90 functions independently of bladder securing means 88 such that bladders 74 and 76 remain overlapped and secured in a substantially circumferential direction if the bladder securing means 88 is not engaged or becomes ineffective while the bladder is inflated to a pressure sufficient to stop arterial blood flow into the limb distal to cuff 58.

Bladder securing means 88 consists of hook material 92 and loop material 70 as shown in FIG. 4 and FIG. 6. Secondary safety securing means 90, forming a separate and independent securing means from bladder securing means 88, is composed of loop material 70, hook material 94, attachment loops 96 and 98, and reinforced thermoplastic rings 100. Rings 100 of secondary safety securing means 90 allow hook material 94 to pivot and engage loop material 70 over a range of angles with respect to the centerline of cuff 58. Rings 100 are D-shaped and are injection moulded from a plastic resin impregnated with reinforcing agents such as glass or carbon fiber. Loops 96 and 98 of secondary safety securing means 90 consist of layers 102 and 104 are fabricated from a thermoplastic polyurethane coated synthetic cloth similar to the material of layer 60.

FIG. 7 illustrates application of overlapping occlusive cuff 58 to substantially conical limb 106. Markings which include label 108 and inflation and alignment guide 110 include markings to restrict use of cuff 58 to properly trained staff, application instructions for securing cuff 58 around limb 106 and instructions detailing proper use of cuff 58 in intravenous regional anesthesia.

Marking means consisting of inflation and alignment guide 110 and label 112 provide information useful to an operator in determining the pressure to which bladders 74 and 76 should be inflated to occlude blood flow. Marking means comprises one element consisting of a set of graduated markings printed on label 112 and another element consisting of a cursor mark located on inflation and alignment guide 110 whereby the value of a preselected parameter is estimated by the juxtaposition of the cursor mark and one of the set of graduated markings when the secondary safety securing means 90 is secured over the overlapping bladders 74 and 76 in a substantially circumferential direction around the limb. Label 112 attached to loop material 70 also includes index markings to identify size range or the maximum and minimum permissible limb circumferences that cuff 58 can be adjusted to fit, and a calibrated scale to indicate a recommended minimum inflation pressure for cuff 58 when applied to limb 106. The recommended minimum inflation pressure corresponds to the lowest constant pressure normally required in cuff 58 to safely and reliably occlude blood flow over a time period suitably long for the performance of a surgical procedure when cuff 58 snugly encircles a normal limb of that circumference in a normotensive subject. This information enables the user to safely apply or determine if another tourniquet cuff size would be more appropriate for the patient and to select a inflation pressure for cuff 58 to reduce the risk of underlying nerve injury and achieve improved patient tolerance of cuff 58 when cuff 58 is pressurized.

Fabrication of the overlapping occlusive cuff 58 proceeds through manufacture of a number of subassemblies. First, layers 60, 62 and 64 are die cut from thermoplastic cloth material. At this time, circular openings are die cut into layers 60 and 62 for later passage of valve port sets 66 and 68.

Label 112, previously silk screened with maximum and minimum permissible limb circumferences and a calibrated scale to indicate a recommended minimum pressure for cuff 58 in enamel ink, is sewn to the loop side of loop material 70. Loop material 70 is sewn to top layer 60 with loops facing away from layer 60. Valve sets 66 and 68 are inserted through the circular openings previously die cut into layer 62, and flanges of valve sets 66 and 68 are bonded to the bottom coated surface of layer 62 through use of radio frequency heat sealing equipment. Layers 60, 62 and 64 are then manipulated such that valve sets 66 and 68, previously bonded to layer 62, pass through the circular openings in layer 60, and the thermoplastic polyurethane coating of layer 60 contacts the upper coated surface of layer 62 and the thermoplastic polyurethane coating of layer 64 contacts the lower coated surface of layer 62. Following this step, layers 60, 62 and 64 are permanently bonded together at the peripheral edge of cuff 58, at the bladder dividing heat seal 78, and at fluid tight seal 118 through use of the radio frequency heat sealing equipment, thereby forming non-inflatable section 114 and inflatable bladder section 116 contained within sheath 61 formed by layers 60 and 64. Partial fluting means 80 bonding layers 60,62 and 64 together using heat seals of either circular or D shaped configuration having an outside diameter of 1.57 cm and inside diameter of 1.19 cm, are formed through use of the radio frequency heat sealing equipment. This completes the fabrication of the first subassembly.

The second subassembly, or secondary safety securing means 90, is fabricated as follows. Labels 108, previously silk screened with text in enamel ink and die cut from nylon cloth material is sewn to the non-hook side of hook material 94. The ends of hook materials 94 of secondary safety securing means 90 are folded over and sewn to provide a small flap for facilitating the release of secondary safety securing means 90 upon completion of the surgical procedure. Assemblies 96 and 98 of secondary safety securing means 90 shown in FIGS. 4 and 6 are constructed by bonding die cut layers 102 and 104 together when the polyurethane coatings of layers 102 and 104 are in contact. Bonded layers 102 and 104 are then passed through rings 100 to form assembly 96 which is sewn to hook material 94 as shown in FIG. 6. Hook material 94 is sewn to assembly 96 such that hooks of material 94 face towards cuff 58.

In final assembly of overlapping occlusive cuff 58, edge trim 82 is first sewn around the perimeter of cuff 58 as shown in FIG. 4. Hook material 92 of bladder securing means 88 is sewn to non-coated surface of layer 64 in section 114 of cuff 58 with hooks facing away from layer 64 as shown in FIGS. 4 and 6. Inflation and alignment guide 110 is sewn to non-coated surface of layer 60 in section 114 of cuff 58. As shown in FIG. 6, secondary safety securing means assembly 90 forming a separate and independent securing means from bladder securing means 88 is completed by passing bonded layers 102 and 104 through rings 100 to form assembly 98 and sewn to layer 60 located in section 114 of cuff 58 such that hooks of material 94 face towards cuff 58. Finally, locking connectors 84 are inserted into valve sets 66 and 68, and tie straps 84 are wrapped and tightened around valves sets 66 and 68 to secure locking connectors 84 in place. This completes fabrication of overlapping occlusive cuff 58.

As shown in FIG. 7, cuff 58 is applied to limb 106 with bladder securing means 88 being fastened followed by secondary safety securing means 90. Bladder securing means 88 is secured around limb 106 by hook material 92 engaging loop material 70. Secondary safety securing means 90 is utilized by pivoting hook material 94 and also engaging loop material 70 such that a maximum contact area is achieved. The arcuate shape of cuff 58 and bladder securing means 88 provides conformance adjustment means for adjusting the shape of cuff 58 over a predefined range of tapers so that cuff 58 remains substantially in contact with limb 106 along the width of cuff 58 and circumference of limb 106. This conformance adjustment means increases resistance of cuff 58 to sudden telescoping down limb 106 due to shape mismatch. Inflation and alignment guide 110 indicates to the user the predefined range of tapers to which cuff 58 can conform by specifying that guide 110 must lie between the proximal and distal edges of cuff 58 when cuff 58 is snugly applied to limb 106. The user references label 112 to obtain the recommended minimum inflation pressure indicated by the position of inflation and alignment guide 110 with respect to calibrated scale of label 112. Should inflation and alignment guide 110 fall outside the calibrated scale on label 112, the user is instructed to select a different size of cuff for the patient. In FIG. 7, cuff 58 is connected by tubing 120 and locking connectors 84 to a pressure source providing gas at a regulated pressure between zero and 500 mmHg. This arrangement provides a means of inflating cuff 58 to apply a desired distribution of pressures to limb 106.

It is to be understood that the invention is not to be limited to the details herein given but may be modified within the scope of the appended claims.

I claim:

1. An overlapping occlusive cuff having secondary safety securing means for improved safety, comprising:
   a) an inflatable bladder for encircling a limb, wherein the length of the bladder is selected to be sufficient for the bladder to encircle the limb at a desired location and have portions that overlap circumferentially around the limb;
   b) bladder securing means for securing the overlapping bladder in a substantially circumferential direction around the limb with the bladder inflated to a pressure sufficient to occlude flow in blood vessels in the limb encircled by the bladder; and
   c) secondary safety securing means superimposed over the overlapped portions of the bladder and superimposed over the bladder securing means, the secondary safety securing means extending in a substantially circumferential direction for securing the overlapping bladder in a substantially circumferential direction around the limb independently of the bladder securing means such that the bladder remains overlapped and secured in a substantially circumferential direction if the bladder securing means is ineffective while the bladder is inflated.

2. A cuff as described in claim 1 and including marking means, wherein the marking means includes one element comprising a set of graduated markings and another element comprising a cursor mark and whereby the value of a preselected parameter is estimated by the juxtaposition of the cursor mark and one of the set of graduated markings when the secondary safety securing means is superimposed over the overlapping bladder in a substantially circumferential direction around the limb.

3. An occlusive cuff, comprising:

an inflatable bladder;

a sheath for containing the bladder, the sheath having side edges extending along the length of the bladder and defining an edge near each end of the bladder;

a substantially flat strap having a first end pivotally connected to the sheath by a ring member thereby to facilitate the extension of the strap into any of a plurality of locations between the side edges of the sheath without twisting the strap out of its substantially flat shape; and securing means for attaching a second end of the strap to the sheath whenever the sheath is curved into a position for encircling a limb.

* * * * *

UNITED STATES PATENT AND TRADEMARK OFFICE
CERTIFICATE OF CORRECTION

PATENT NO. : 5,312,431

DATED : May 17, 1994

INVENTOR(S) : James A. McEwen

It is certified that error appears in the above-indentified patent and that said Letters Patent is hereby corrected as shown below:

Column 3, line 24, "bee" should be --been--;

Column 4, line 36, "sam" should be --same--;

Column 4, line 50, "inflated" should be --inflated.--;

Column 6, line 48, "inflated" should be --inflated.--;

Column 9, line 51, "operator" should be --operator.--;

Column 9, line 57, "inflated" should be --inflated.--;

UNITED STATES PATENT AND TRADEMARK OFFICE
CERTIFICATE OF CORRECTION

PATENT NO. : 5,312,431
DATED : May 17, 1994
INVENTOR(S) : James A. McEwen

It is certified that error appears in the above-indentified patent and that said Letters Patent is hereby corrected as shown below:

Column 10, line 22, "subject" should be --subject.--;

Column 11, line 16, "material 30" should be --material 20.--;

Column 14, line 67, "a" should be --an--.

In the Claims:

Column 18, line 1, "an edge" should be --an end edge--.

Signed and Sealed this

Sixth Day of September, 1994

Attest:

BRUCE LEHMAN

*Attesting Officer*  *Commissioner of Patents and Trademarks*